US008039013B2

(12) United States Patent
Dahmen et al.

(10) Patent No.: US 8,039,013 B2
(45) Date of Patent: Oct. 18, 2011

(54) SYNERGISTIC FUNGIDICAL ACTIVE SUBSTANCE COMBINATIONS

(75) Inventors: Peter Dahmen, Neuss (DE); Ulrike Wachendorff-Neumann, Neuwied (DE); Ralf Dunkel, Lyons (FR)

(73) Assignee: Bayer CropScience AG, Monheim (DE)

(*) Notice: Subject to any disclaimer, the term of this patent is extended or adjusted under 35 U.S.C. 154(b) by 928 days.

(21) Appl. No.: 11/575,470

(22) PCT Filed: Sep. 3, 2005

(86) PCT No.: PCT/EP2005/009503
§ 371 (c)(1),
(2), (4) Date: Aug. 1, 2007

(87) PCT Pub. No.: WO2006/032356
PCT Pub. Date: Mar. 30, 2006

(65) Prior Publication Data
US 2008/0269263 A1  Oct. 30, 2008

(30) Foreign Application Priority Data
Sep. 17, 2004 (DE) .......................... 10 2004 045 242

(51) Int. Cl.
*A01N 25/00* (2006.01)
*A01N 43/26* (2006.01)
(52) U.S. Cl. ........ 424/405; 424/406; 514/383; 514/384; 514/386; 514/462
(58) Field of Classification Search ........................ None
See application file for complete search history.

(56) References Cited

U.S. PATENT DOCUMENTS

| | | | |
|---|---|---|---|
| 5,439,926 A * | 8/1995 | Dutzmann et al. | 514/383 |
| 6,306,850 B1 * | 10/2001 | Dutzmann et al. | 514/229.2 |
| 2007/0060579 A1 * | 3/2007 | Wachendorff-Neumann et al. | 514/229.2 |
| 2007/0293550 A1 | 12/2007 | Rochling et al. | |
| 2007/0298966 A1 | 12/2007 | Fischer et al. | |
| 2008/0139389 A1 | 6/2008 | Kneen et al. | |
| 2008/0269051 A1 | 10/2008 | Suty-Heinze et al. | |
| 2009/0018015 A1 * | 1/2009 | Wachendorff-Neumann et al. | 504/100 |
| 2009/0069178 A1 | 3/2009 | Suty-Heinze et al. | |
| 2009/0170918 A1 | 7/2009 | Wolf | |
| 2009/0286681 A1 | 11/2009 | Dahmen et al. | |
| 2009/0306109 A1 | 12/2009 | Dutzmann et al. | |
| 2010/0063039 A1 | 3/2010 | Häuser-Hahn et al. | |
| 2010/0145045 A1 | 6/2010 | Häuser-Hahn et al. | |
| 2011/0003688 A1 | 1/2011 | Hungenberg et al. | |
| 2011/0034496 A1 | 2/2011 | Häuser-Hahn et al. | |
| 2011/0064827 A1 | 3/2011 | Seitz et al. | |
| 2011/0124501 A1 | 5/2011 | Cristau et al. | |
| 2011/0160053 A1 | 6/2011 | Wachendorff-Neumann et al. | |
| 2011/0166109 A1 | 7/2011 | Andersch et al. | |

FOREIGN PATENT DOCUMENTS

| | | |
|---|---|---|
| EP | 0 627 163 A1 | 12/1994 |
| GB | 2176106 A | 12/1986 |
| GB | 2 262 037 A | 6/1993 |
| WO | WO 96/38040 A1 | 12/1996 |
| WO | WO 96/41533 A1 | 12/1996 |
| WO | WO 98/47367 A1 | 10/1998 |
| WO | WO 01/37666 A2 | 5/2001 |
| WO | WO 2005/034628 A1 | 4/2005 |
| WO | WO 2005/039294 A1 | 5/2005 |
| WO | WO 2005/041653 A2 | 5/2005 |
| WO | WO 2005/046331 A1 | 5/2005 |
| ZA | 9604371 A | 12/1996 |
| ZA | 9604833 A | 1/1997 |
| ZA | 2002/02981 | 6/2003 |

OTHER PUBLICATIONS

International Search Report for International Application No. PCT/EP2005/009503, European Patent Office, Netherlands, mailed on Dec. 15, 2005.
Bauer, T.A., et al., "Response of Selected Weed Species to Postemergence Imazethapyr and Bentazon," *Weed Tech.* 9:236-242, The Weed Science Society of America (1995).
Blackshaw, R.E., "HOW-39866 Use in Chemical Fallow Systems," *Weed Tech.* 3:420-428, The Weed Science Society of America (1989).
Blackshaw, R.E., "Synergistic Mixes of DPX-A7881 and Clopyralid in Canola (*Brassica napus*)," *Weed Tech.* 3:690-695, The Weed Science Society of America (1989).
Blackshaw, R.E., et al., "Herbicide Combinations for Postemergent Weed control in Safflower (*Carthamus tinctorius*)," *Weed Tech.* 4:97-104, The Weed Science Society of America (1990).
Blouin, D.C., et al., "Analysis of Synergistic and Antagonistic Effects of Herbicides Using Nonlinear Mixed-Model Methodology," *Weed Tech.* 18:464-472, The Weed Science Society of America (2004).
Bradley, P.R., et al., "Response of Sorghum (*Sorghum bicolor*) to Atrazine, Ammonium Sulfate, and Glyphosate," *Weed Tech.* 14:15-18, The Weed Science Society of America (2000).
Buker, III, R.S., et al., "Confirmation and Control of a Paraquat-Tolerant Goosegrass (*Eleusine indica*) Biotype," *Weed Tech.* 16:309-313, The Weed Science Society of America (2002).
Burke, I.C., et al., "CGA-362622 Antagonizes Annual Grass Control with Clethodim," *Weed Tech.* 16:749-754, The Weed Science Society of America (2002). Colby, S.R., "Calculating Synergistic and Antagonistic Responses of Herbicide Combinations," *Weeds* 15:20-22, Weed Society of America (1967).
Flint, J.L., et al., "Analyzing Herbicide Interactions: A Statistical Treatment of Colby's Method," *Weed Tech.* 2:304-309, The Weed Science Society of America (1988).
Gillespie, G.R., and Nalewaja, J.D., "Wheat (*Triticum aestivum*) Response to Triallate Plus Chlorsulfuron," *Weed Tech.* 3:20-23, The Weed Science Society of America (1989).
Green, J.M., et al., "Metribuzin and Chlorimuron Mixtures for Preemergence Broadleaf Weed Control in Soybeans, *Glycine max*," *Weed Tech.* 2:355-363, The Weed Science Society of America (1988).
Harker, N.K., and O'Sullivan, P.A., "Synergistic Mixtures of Sethoxydim and Fluazifop on Annual Grass Weeds," *Weed Tech.* 5:310-316, The Weed Science Society of America (1991).
Kent, L.M., et al., "Effect of Ammonium Sulfate, Imazapyr, and Environment on the Phytotoxicity of Imazethapyr," *Weed Tech.* 5:202-205, The Weed Science Society of America (1991).

(Continued)

*Primary Examiner* — Neil Levy
(74) *Attorney, Agent, or Firm* — Sterne, Kessler, Goldstein & Fox P.L.L.C.

(57) ABSTRACT

The present invention relates to novel active substance combinations which contain spiroxamine, which is known, a known azole and a known carboxamide and which are very suitable for controlling undesired phytopathogenic fungi.

18 Claims, No Drawings

OTHER PUBLICATIONS

Kotoula-Syka, E., et al., "Interactions between SAN 582H and Selected Safeners on Grain Sorghum (*Sorghum bicolor*) and Corn (*Zea mays*)," *Weed Tech.* 10:299-304, The Weed Science Society of America (1996).

Lanclos, D.Y., et al., "Glufosinate Tank-Mix Combinations in Glufosinate-REsistant Rice (*Oryza sativa*)," *Weed Tech.* 16:659-663, The Weed Science Society of America (2002).

Norris, J.L., et al., "Weed Control from Herbicide Combinations with Three Formulations of Glyphosate," *Weed Tech.* 15:552-558, The Weed Science Society of America (2001).

Novosel, K.M., et al., "Metolachlor Efficacy as Influenced by Three Acetolactate Synthase-Inhibiting Herbicides," *Weed Tech.* 12:248-253, The Weed Science Society of America (1998).

Palmer, E.W., et al., "Broadleaf Weed Control in Soybean (*Glycine max*) with CGA-277476 and Four Postemergence Herbicides," *Weed Tech.* 14:617-623, The Weed Science Society of America (2000).

Rummens, F.H.A., "An Improved Definition of Synergistic and Antagonistic Effects," *Weed Science* 23(1):4-6, The Weed Science Society of America, United States (1975).

Salzman, F.P., and Renner, K.A., "Response of Soybean Combinations of Clomazone, Metribuzin, Linuron, Alachlor, and Atrazine," *Weed Tech.* 6:922-929, The Weed Science Society of America (1992).

Scott, R.C., et al., "Spray Adjuvant, Formulation, and Environmental Effects on Synergism from Post-Applied Tank Mixtures of SAN 582H with Fluazifop-P, Imazethapyr, and Sethoxydim," *Weed Tech.* 12:463-469, The Weed Science Society of America (1998).

Shaw, D.R. and Arnold, J.C., "Weed Control from Herbicide Combinations with Glyphosate," *Weed Tech.* 16:1-6, The Weed Science Society of America (2002).

Snipes, C.E., and Allen, R.L., "Interaction of Graminicides Applied in Combination with Pyrithiobac," *Weed Tech.* 10:889-892, The Weed Science Society of America (1996).

Sun, Y.-P, & Johnson, E.R., "Analysis of Joint Action of Insecticides against House Flies", *J. Econ. Entomol.*, 53:887-892, United States (1960).

Tomlin, C., ed, *The Pesticide Manual*, 1242-1245, British Crop Protection Council, Farnham, UK (1997).

Wehtje, G. and Walker, R.H., "Interaction of Glyphosate and 2,4-DB for the Control of Selected Morningglory (*Ipomoea* spp.) Species," *Weed Tech.* 11:152-156, The Weed Science Society of America (1997).

Zhang, W., et al., "Fenoxaprop Interactions for Barnyardgrass (*Echinochloa crus-galli*) Control in Rice," *Weed Tech.* 19:293-297, The Weed Science Society of America (2005).

Opposition Proceedings in European Patent No. EP-B-1482798, Mar. 5, 2007-Nov. 9, 2009.

Prosecution History of European Patent Appl. No. 03735610.2 (European Counterpart of U.S. Appl. No. 10/518,742), Jul. 13, 2006-Sep. 25, 2009.

Partial English language translation of Prosecution History of European Patent Appl. No. 03735610.2, Jul. 13, 2006-Sep. 25, 2009.

Partial English language translation of Opposition Proceeding in European Patent No. EP-B-1482798, Feb. 26, 2007-Nov. 9, 2009.

"Azoxystrobin data sheet," Compendium of Pesticide Common Names, accessed at http://www.alanwood.net/pesticides/azoxystrobin.html, accessed on Apr. 8, 2009, 1 page.

"Kresoxim-methyl data sheet," Compendium of Pesticide Common Names, accessed at http://www.alanwood.net/pesticides/kresoxim-methyl.html, accessed on Apr. 8, 2009, 1 page.

"Metominostrobin data sheet," Compendium of Pesticide Common Names, accessed at http://www.alanwood.net/pesticides/metominostrobin.html, accessed on Apr. 8, 2009, 1 page.

Office Action mailed Jul. 19, 2010, in U.S. Appl. No. 10/573,066, Wachendorff-Neumann et al., filed Oct. 24, 2006.

Office Action mailed Dec. 30, 2009, in U.S. Appl. No. 10/573,066, Wachendorff-Neumann et al., filed Oct. 24, 2006.

Office Action mailed Jun. 16, 2009, in U.S. Appl. No. 10/573,066, Wachendorff-Neumann et al., filed Oct. 24, 2006.

Office Action mailed Oct. 15, 2008, in U.S. Appl. No. 10/573,066, Wachendorff-Neumann et al., filed Oct. 24, 2006.

Co-pending, U.S. Appl. No. 12/929,640 inventors Ebbinghaus, D., et al., filed on Feb. 4, 2011 (Not Published).

Co-pending, U.S. Appl. No. 13/087,144 inventors Ebbinghaus, D., et al., filed on Apr. 14, 2011 (Not Published).

Co-pending, U.S. Appl. No. 13/061,976 inventors Münks, K.-W., et al., international filed Aug. 21, 2009 (Not Published).

\* cited by examiner

SYNERGISTIC FUNGICIDAL ACTIVE SUBSTANCE COMBINATIONS

This application is a National Stage of International Application No. PCT/EP2005/009503, filed Sep. 3, 2005, which claims the benefit of German Patent Application No. 10 2004 045 242.3, filed Sep. 17, 2004. The entirety of each of these applications is incorporated by reference herein.

The present invention relates to novel active substance combinations which contain spiroxamine, which is known, a known azole and a known carboxamide and which are very suitable for controlling undesired phytopathogenic fungi.

It has already been disclosed that N-[(8-tert-butyl-1,4-dioxaspiro[4.5]dec-2-yl)methyl]-N-ethylpropan-1-amine (spiroxamine), certain azoles such as, for example, 1-(4-chlorophenyl)-4,4-dimethyl-3-(1H-1,2,4-triazol-1-ylmethyl)pentan-3-ol (tebuconazole) and 2-[2-(1-chlorocyclopropyl)-3-(2-chlorophenyl)-2-hydroxypropyl]-2,4-dihydro-3H-1,2,4-triazole-3-thione (prothioconazole), and certain carboxamides such as, for example, N-[2-(1,3-dimethylbutyl)phenyl]-5-fluoro-1,3-dimethyl-1H-pyrazole-4-carboxamide and N-(3',4'-dichloro-5-fluoro-1,1'-biphenyl-2-yl)-3-(difluoromethyl)-1-methyl-1H-pyrazole-4-carboxamide, have fungicidal properties (cf. EP-A 0281 842, EP-A 0 040 345, WO 96/16048, WO 03/010149 and WO 03/070705).

It is furthermore known that mixtures of spiroxamine and azoles, or of spiroxamine and carboxamides, or of azoles and carboxamides, can be employed for controlling fungi in plant protection (cf. EP-A 0 627 163, WO 98/47367, DE-A 103 49 501 and DE-A 103 47 090).

Both the activity of the individual components and the activity of the known mixtures of in each case two active substances is good, but leaves something to be desired in some cases when low rates of application are used.

There have now been found novel active substance combinations with very good fungicidal properties, comprising (A) N-[(8-tert-butyl-1,4-dioxaspiro[4.5]dec-2-yl)methyl]-N-ethylpropan-1-amine (spiroxamine), of the formula (I)

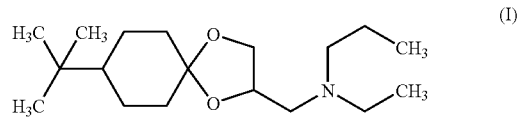

and
(B) an azole of the general formula (II)

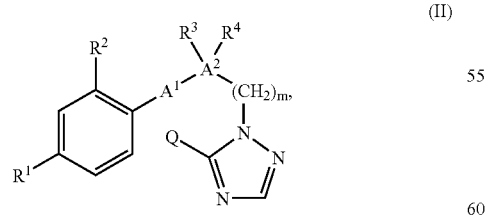

in which
Q represents hydrogen or SH,
m represents 0 or 1,
$R^1$ represents hydrogen, fluorine, chlorine, phenyl or 4-chlorophenoxy,
$R^2$ represents hydrogen or chlorine,
$A^1$ represents a direct bond, —$CH_2$—, —$(CH_2)_2$— or —O—,
$A^1$ furthermore represents *—$CH_2$—$CHR^5$— or *—CH=$CR^5$—, where the bond marked * is linked to the phenyl ring, and
$R^3$ and $R^5$ in this case together represent —$CH_2$—$CH_2$—CH[CH($CH_3$)$_2$]— or —$CH_2$—$CH_2$—C($CH_3$)$_2$—,
$A^2$ represents C or Si (silicon),
$A^1$ furthermore represents —N($R^5$)— and $A^2$ furthermore together with $R^3$ and $R^4$ represents the group C=N—$R^6$, where $R^5$ and $R^6$ in this case together represent the group

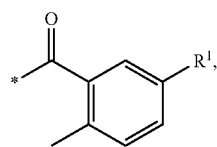

where the bond marked * is linked to $R^5$,
$R^3$ represents hydrogen, hydroxyl or cyano,
$R^4$ represents 1-cyclopropylethyl, 1-chlorocyclopropyl, $C_1$-$C_4$-alkyl, $C_1$-$C_6$-hydroxyalkyl, $C_1$-$C_4$-alkylcarbonyl, $C_1$-$C_2$-haloalkoxy-$C_1$-$C_2$-alkyl, trimethylsilyl-$C_1$-$C_2$-alkyl, monofluorophenyl or phenyl,
$R^3$ and $R^4$ furthermore together represent —O—$CH_2$—CH($R^6$)—O—, —O—$CH_2$—CH($R^6$)—$CH_2$— or —O—CH-(2-chlorophenyl)-,
$R^6$ represents hydrogen, $C_1$-$C_4$-alkyl or bromine;
and
(C) a carboxamide of the general formula (III)

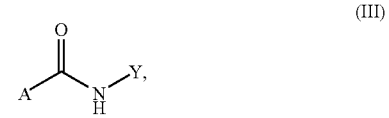

in which
A represents one of the following radicals A1 to A8:

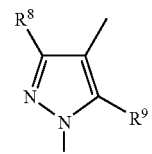

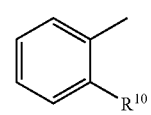

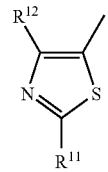

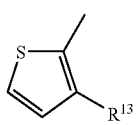 A4

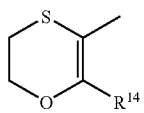 A5

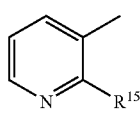 A6

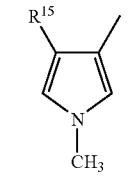 A7

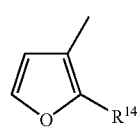 A8

$R^7$ represents methyl, ethyl, n- or isopropyl,
$R^8$ represents iodine, methyl, difluoromethyl or trifluoromethyl,
$R^9$ represents hydrogen, fluorine, chlorine or methyl,
$R^{10}$ represents chlorine, bromine, iodine, methyl, difluoromethyl or trifluoromethyl,
$R^{11}$ represents hydrogen, chlorine, methyl, amino or dimethylamino,
$R^{12}$ represents methyl, difluoromethyl or trifluoromethyl,
$R^{13}$ represents bromine or methyl,
$R^{14}$ represents methyl or trifluoromethyl,
$R^{15}$ represents chlorine or trifluoromethyl,
Y represents one of the following radicals Y1 to Y4:

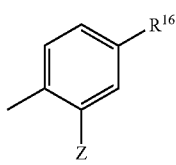 Y1

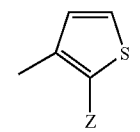 Y2

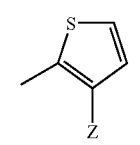 Y3

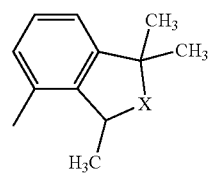 Y4

$R^{16}$ represents hydrogen or fluorine,
X represents —CH$_2$— or O (oxygen),
Z represents one of the following radicals Z1 or Z2:

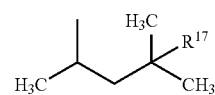 Z1

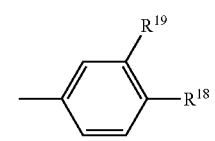 Z2

$R^{17}$ represents hydrogen, fluorine, chlorine, methyl, ethyl, n-, isopropyl, monofluoromethyl, difluoromethyl, trifluoromethyl, monochloromethyl, dichloromethyl or trichloromethyl,
$R^{18}$ represents fluorine, chlorine, bromine, methyl, trifluoromethyl, trifluoromethoxy, —CH=N—OMe or —C(Me)=N—OMe,
$R^{19}$ represents hydrogen, fluorine, chlorine, bromine, methyl or trifluoromethyl.

Surprisingly, the fungicidal activity of the active substance combinations according to the invention far exceeds the total of the activities of the individual active substances or the activity of the known two-way mixtures. A genuine synergistic effect which could not have been predicted therefore exists, not simply a complementation of action.

Formula (II) comprises the following preferred mixing partners from the group of the azoles:
(II-1) azaconazole (disclosed in DE-A 25 51 560), of the formula

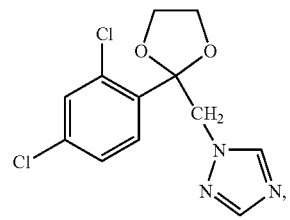

(II-2) etaconazole (disclosed in DE-A 25 51 560), of the formula

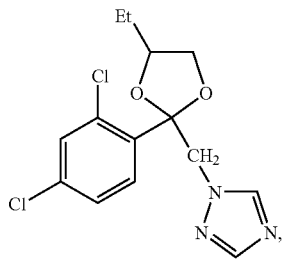

(II-3) propiconazole (disclosed in DE-A 25 51 560), of the formula

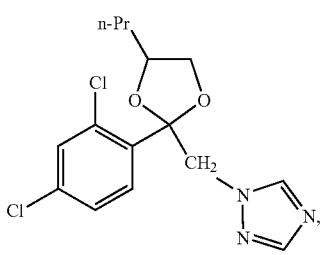

(II-4) difenoconazole (disclosed in EP-A 0 112 284), of the formula

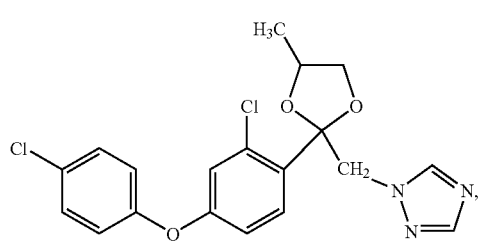

(II-5) bromuconazole (disclosed in EP-A 0 258 161), of the formula

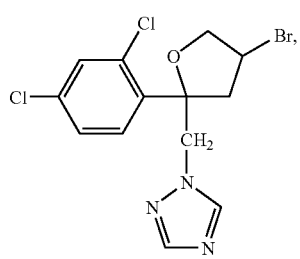

(II-6) cyproconazole (disclosed in DE-A 34 06 993), of the formula

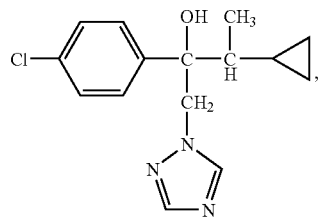

(II-7) hexaconazole (disclosed in DE-A 30 42 303), of the formula

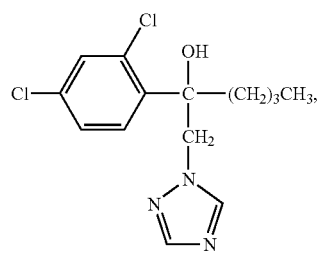

(II-8) penconazole (disclosed in DE-A 27 35 872), of the formula

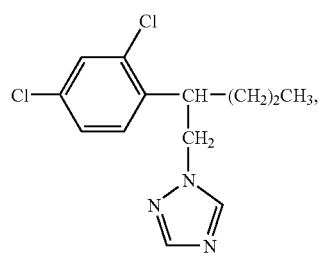

(II-9) myclobutanil (disclosed in EP-A 0 145 294), of the formula

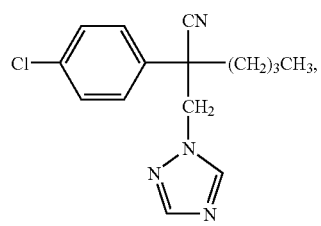

(II-10) tetraconazole (disclosed in EP-A 0 234 242), of the formula

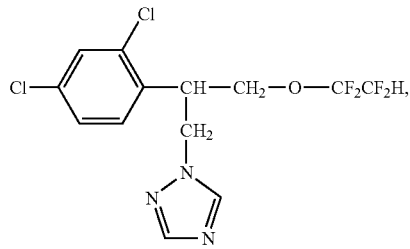

(II-11) flutriafol (disclosed in EP-A 0 015 756), of the formula

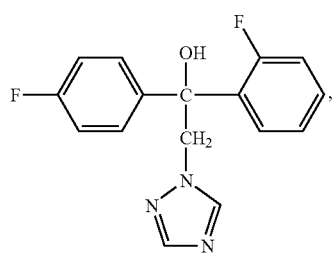

(II-12) epoxiconazole (disclosed in EP-A 0 196 038), of the formula

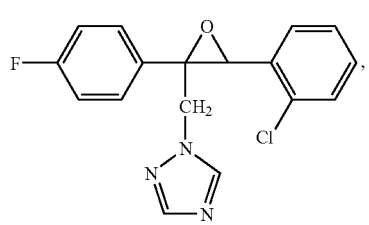

(II-13) flusilazole (disclosed in EP-A 0 068 813), of the formula

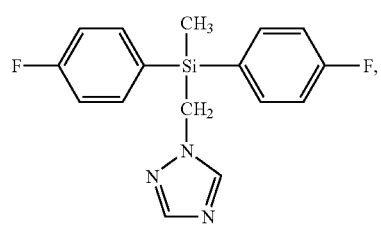

(II-14) simeconazole (disclosed in EP-A 0 537 957), of the formula

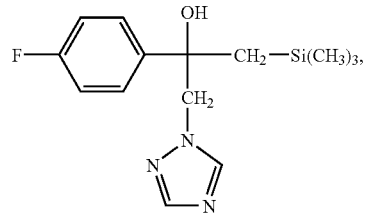

(II-15) prothioconazole (disclosed in WO 96/16048), of the formula

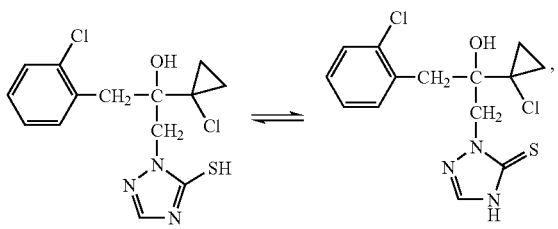

(II-16) fenbuconazole (disclosed in DE-A 37 21 786), of the formula

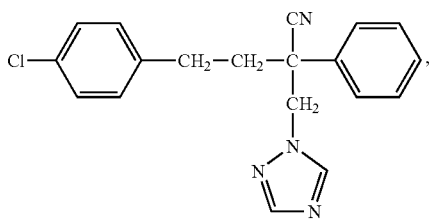

(II-17) tebuconazole (disclosed in EP-A 0 040 345), of the formula

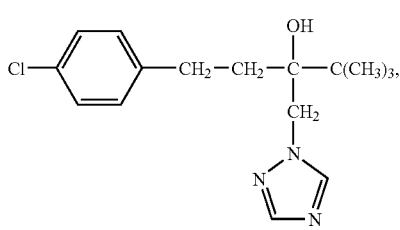

(II-18) ipconazole (disclosed in EP-A 0 329 397), of the formula

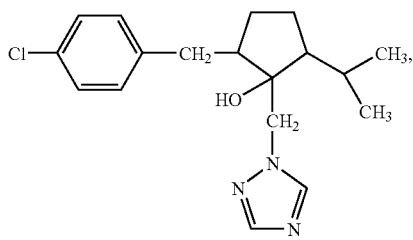

(II-19) metconazole (disclosed in EP-A 0 329 397), of the formula

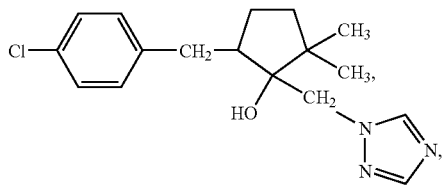

(II-20) triticonazole (disclosed in EP-A 0 378 953), of the formula

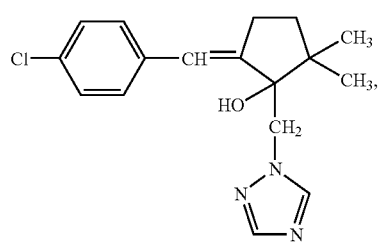

(II-21) bitertanol (disclosed in DE-A 23 24 010), of the formula

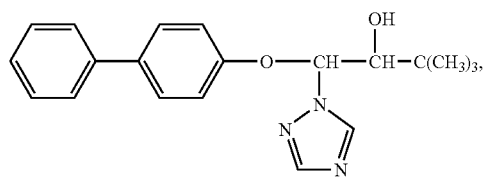

(II-22) triadimenol (disclosed in DE-A 23 24 010), of the formula

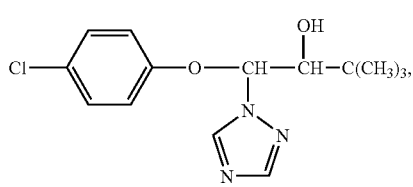

(II-23) triadimefon (disclosed in DE-A 22 01 063), of the formula

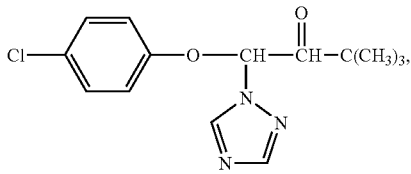

(II-24) fluquinconazole (disclosed in EP-A 0 183 458), of the formula (II-25) quinconazole (disclosed in EP-A 0 183 458), of the formula Formula (II) comprises the following especially preferred mixing partners from the group of the azoles:
(II-3) propiconazole
(II-4) difenoconazole
(II-6) cyproconazole
(II-7) hexaconazole
(II-8) penconazole
(II-9) myclobutanil
(II-10) tetraconazole
(II-12) epoxiconazole
(II-13) flusilazole
(II-15) prothioconazole
(II-16) fenbuconazole
(II-17) tebuconazole
(II-19) metconazole
(II-21) bitertanol
(II-22) triadimenol
(II-23) triadimefon
(II-24) fluquinconazole Formula (II) comprises the following very especially preferred mixing partners from the group of the azoles:
(II-15) prothioconazole
(II-17) tebuconazole
(II-21) bitertanol
(II-22) triadimenol
(II-24) fluquinconazole- Formula (II) comprises the following particularly preferred mixing partners from the group of the azoles:
(II-15) prothioconazole
(II-17) tebuconazole
(II-24) fluquinconazole Formula (III) comprises the following preferred mixing partners from the group of the carboxamides:

(III-1) N-[2-(1,3-dimethylbutyl)phenyl]-1,3-dimethyl-1H-pyrazole-4-carboxamide (disclosed in JP-A 10-251240), of the formula

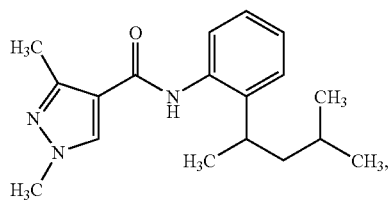

(III-2) N-[2-(1,3-dimethylbutyl)phenyl]-5-fluoro-1,3-dimethyl-1H-pyrazole-4-carboxamide (disclosed in WO 03/010149), of the formula

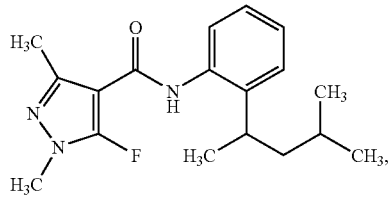

(III-3) N-[2-(1,3-dimethylbutyl)phenyl]-5-chloro-1,3-dimethyl-1H-pyrazole-4-carboxamide (disclosed in JP-A 10-251240), of the formula

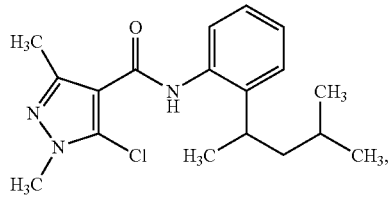

(III-4) 3-(difluoromethyl)-N-[2-(1,3-dimethylbutyl)phenyl]-1-methyl-1H-pyrazole-4-carboxamide, of the formula

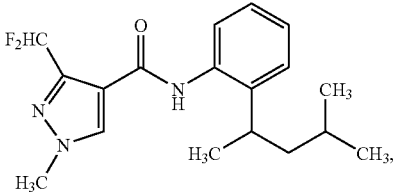

(III-5) 3-(trifluoromethyl)-N-[2-(1,3-dimethylbutyl)phenyl]-5-fluoro-1-methyl-1H-pyrazole-4-carboxamide (disclosed in WO 2004/067515), of the formula

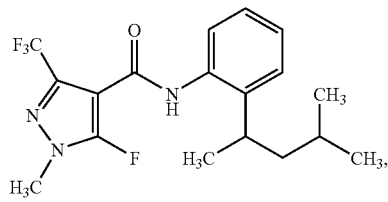

(III-6) 3-(trifluoromethyl)-N-[2-(1,3-dimethylbutyl)phenyl]-5-chloro-1-methyl-1H-pyrazole-4-carboxamide (disclosed in JP-A 10-251240), of the formula

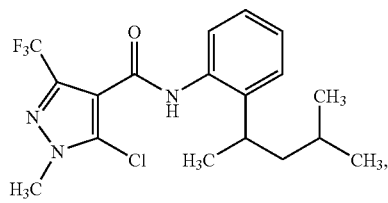

(III-7) 1,3-dimethyl-N-[2-(1,3,3-trimethylbutyl)phenyl]-1H-pyrazole-4-carboxamide, of the formula

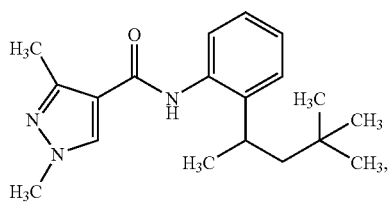

(III-8) 5-fluoro-1,3-dimethyl-N-[2-(1,3,3-trimethylbutyl)phenyl]-1H-pyrazole-4-carboxamide (disclosed in WO 03/010149), of the formula

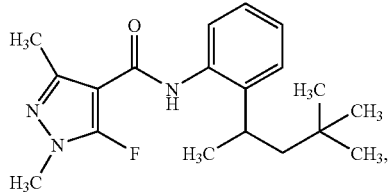

(III-9) 3-(difluoromethyl)-1-methyl-N-[2-(1,3,3-trimethylbutyl)phenyl]-1H-pyrazole-4-carboxamide, of the formula

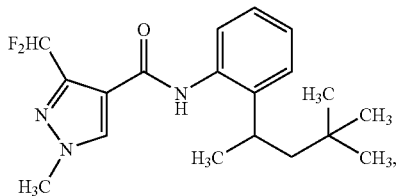

(III-10) 3-(trifluoromethyl)-1-methyl-N-[2-(1,3,3-trimethylbutyl)phenyl]-1H-pyrazole-4-carboxamide, of the formula

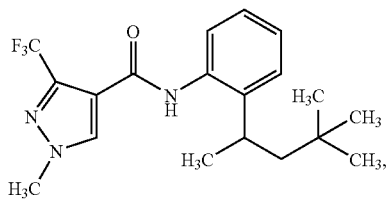

(III-11) 3-(trifluoromethyl)-5-fluoro-1-methyl-N-[2-(1,3,3-trimethylbutyl)phenyl]-1H-pyrazole-4-carboxamide (disclosed in WO 2004/067515), of the formula

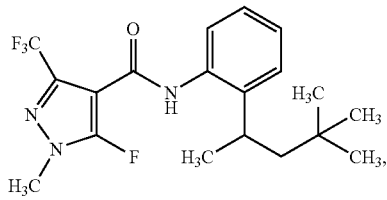

(III-12) 3-(trifluoromethyl)-5-chloro-1-methyl-N-[2-(1,3,3-trimethylbutyl)phenyl]-1H-pyrazole-4-carboxamide, of the formula

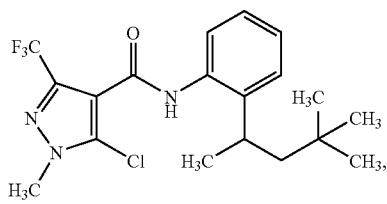

(III-13) N-[2-(1,3-dimethylbutyl)phenyl]-2-iodobenzamide (disclosed in WO 2004/005242), of the formula

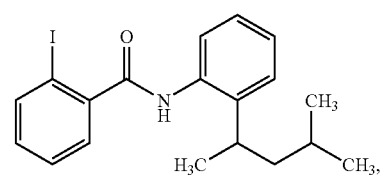

(III-14) 2-iodo-N-[2-(1,3,3-trimethylbutyl)phenyl]benzamide (disclosed in WO 2004/005242), of the formula

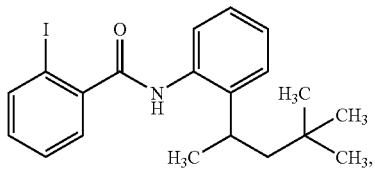

(III-15) N-[2-(1,3-dimethylbutyl)phenyl]-2-(trifluoromethyl)benzamide (disclosed in WO 2004/005242), of the formula

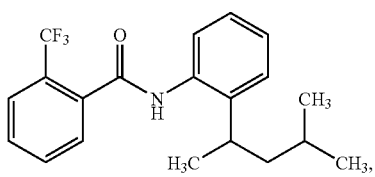

(III-16) 2-(trifluoromethyl)-N-[2-(1,3,3-trimethylbutyl)phenyl]benzamide (disclosed in WO 2004/005242), of the formula

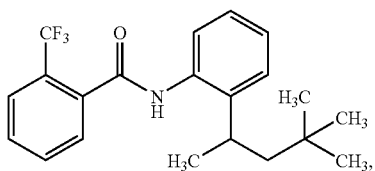

(III-17) 2-chloro-N-(1,1,3-trimethylindan-4-yl)nicotinamide (disclosed in EP-A 0 256 503), of the formula

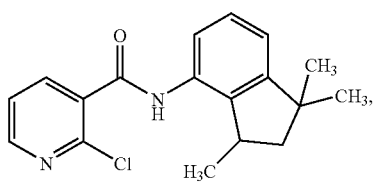

(III-18) boscalid (disclosed in DE-A 195 31 813), of the formula

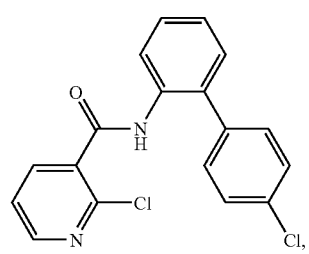

(III-19) furametpyr (disclosed in EP-A 0 315 502), of the formula

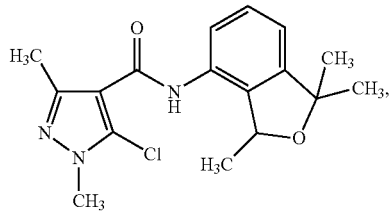

(III-20) N-(3-p-tolylthiophen-2-yl)-1-methyl-3-trifluoromethyl-1H-pyrazole-4-carboxamide (disclosed in EP-A 0 737 682), of the formula

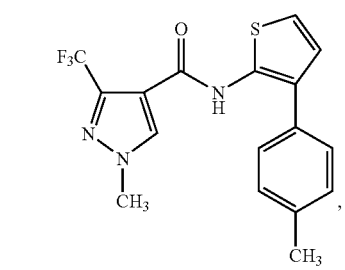

(III-21) penthiopyrad (disclosed in EP-A 0 737 682), of the formula

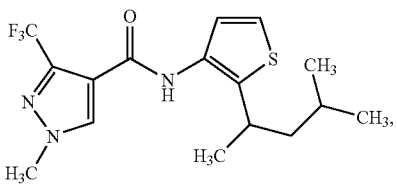

(III-22) N-[2-(1,3-dimethylbutyl)phenyl]-1-methyl-4-(trifluoromethyl)-1H-pyrrole-3-carboxamide (disclosed in WO 02/38542), of the formula

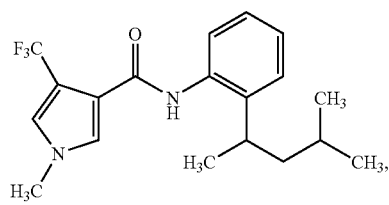

(III-23) N-(3',4'-dichloro-5-fluoro-1,1'-biphenyl-2-yl)-3-(difluoromethyl)-1-methyl-1H-pyrazole-4-carboxamide (disclosed in WO 03/070705), of the formula

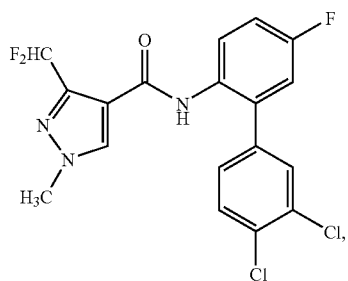

(III-24) 3-(difluoromethyl)-N-{3'-fluoro-4'-[(E)-(methoxyimino)methyl]-1,1'-biphenyl-2-yl}-1-methyl-1H-pyrazole-4-carboxamide (disclosed in WO 02/08197), of the formula

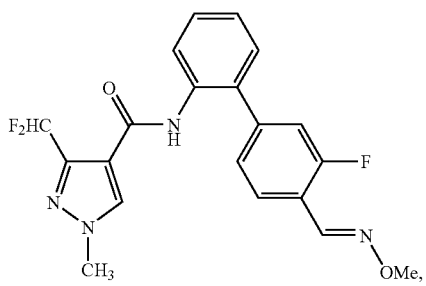

(III-25) 3-(trifluoromethyl)-N-{3'-fluoro-4'-[(E)-(methoxyimino)methyl]-1,1'-biphenyl-2-yl}-1-methyl-1H-pyrazole-4-carboxamide (disclosed in WO 02/08197), of the formula

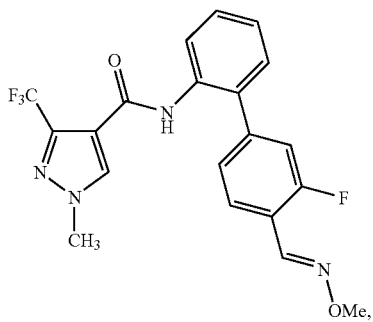

(III-26) N-(3',4'-dichloro-1,1'-biphenyl-2-yl)-5-fluoro-1,3-dimethyl-1H-pyrazole-4-carboxamide (disclosed in WO 00/14701), of the formula

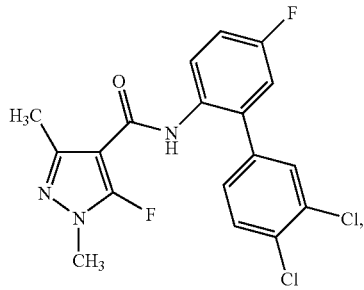

(III-27) N-(4'-chloro-3'-fluoro-1,1'-biphenyl-2-yl)-2-methyl-4-(trifluoromethyl)-1,3-thiazole5-carboxamide (disclosed in WO 03/066609), of the formula

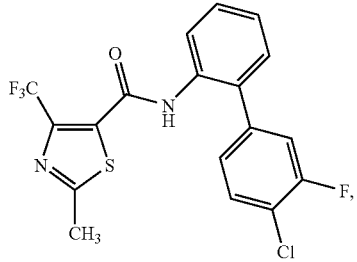

(III-28) N-(4'-chloro-1,1'-biphenyl-2-yl)-4-(difluoromethyl)-2-methyl-1,3-thiazole-5-carboxamide (disclosed in WO 03/066610), of the formula

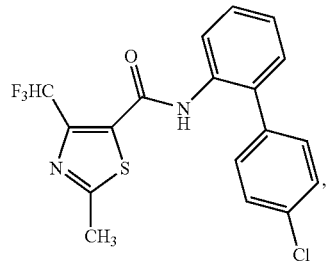

(III-29) N-(4'-bromo-1,1'-biphenyl-2-yl)-4-(difluoromethyl)-2-methyl-1,3-thiazole-5-carboxamide (disclosed in WO 03/066610), of the formula

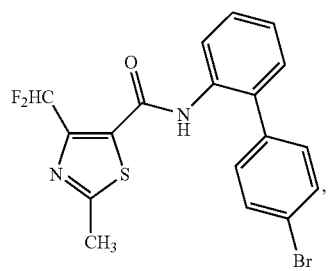

(III-30) 4-(difluoromethyl)-2-methyl-N-[4'-(trifluoromethyl)-1,1'-biphenyl-2-yl]-1,3-thiazole-5-carboxamide (disclosed in WO 03/066610), of the formula

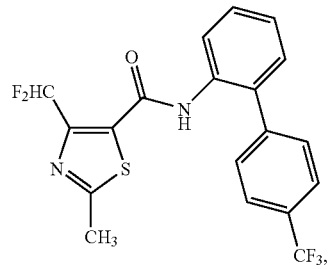

(III-31) N-(4'-iodo-1,1'-biphenyl-2-yl)-4-(difluoromethyl)-2-methyl-1,3-thiazole-5-carboxamide (disclosed in WO 03/066610), of the formula

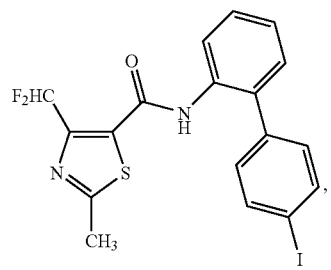

(III-32) N-(4'-chloro-3'-fluoro-1,1'-biphenyl-2-yl)-2-methyl-4-(difluoromethyl)-1,3-thiazole-5-carboxamide (disclosed in WO 03/066610), of the formula

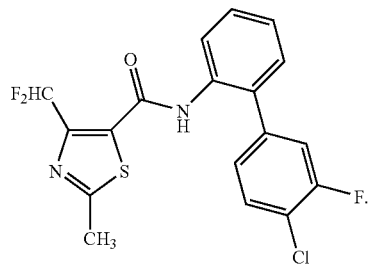

Formula (III) comprises the following especially preferred mixing partners from the group of the carboxamides:
(III-2) N-[2-(1,3-dimethylbutyl)phenyl]-5-fluoro-1,3-dimethyl-1H-pyrazole-4-carboxamide
(III-5) 3-(trifluoromethyl)-N-[2-(1,3-dimethylbutyl)phenyl]-5-fluoro-1-methyl-1H-pyrazole-4-carboxamide
(III-8) 5-fluoro-1,3-dimethyl-N-[2-(1,3,3-trimethylbutyl)phenyl]-1H-pyrazole-4-carboxamide
(III-13) N-[2-(1,3-dimethylbutyl)phenyl]-2-iodobenzamide
(III-15) N-[2-(1,3-dimethylbutyl)phenyl]-2-(trifluoromethyl)benzamide
(III-18) boscalid
(III-19) furametpyr
(III-21) penthiopyrad
(III-22) N-[2-(1,3-dimethylbutyl)phenyl]-1-methyl-4-(trifluoromethyl)-1H-pyrrole-3-carboxamide
(III-23) N-(3',4'-dichloro-5-fluoro-1,1'-biphenyl-2-yl)-3-(difluoromethyl)-1-methyl-1H-pyrazole-4-carboxamide (III-24) 3-(difluoromethyl)-N-{3'-fluoro-4'-[(E)-(methoxy-imino)methyl]-1,1'-biphenyl-2-yl}-1-methyl-1H-pyrazole-4-carboxamide (III-25) 3-(trifluoromethyl)-N-{3'-fluoro-4'-[(E)-(methoxy-imino)methyl]-1,1'-biphenyl-2-yl}-1-methyl-1H-pyrazole-4-carboxamide (III-26) N-(3',4'-dichloro-1,1'-biphenyl-2-yl)-5-fluoro-1,3-dimethyl-1H-pyrazole-4-carboxamide (III-29) N-(4'-bromo-1,1'-biphenyl-2-yl)-4-(difluoromethyl)-2-methyl-1,3-thiazole-5-carboxamide (III-31) N-(4'-iodo-1,1'-biphenyl-2-yl)-4-(difluoromethyl)-2-methyl-1,3-thiazole-5-carboxamide (III-32) N-(4'-chloro-3'-fluoro-1,1'-biphenyl-2-yl)-2-methyl-4-(difluoromethyl)-1,3-thiazole-5-carboxamide Formula (III) comprises the following very especially preferred mixing partners from the group of the carboxamides:

(III-2) N-[2-(1,3-dimethylbutyl)phenyl]-5-fluoro-1,3-dimethyl-1H-pyrazole-4-carboxamide (III-8) 5-fluoro-1,3-dimethyl-N-[2-(1,3,3-trimethylbutyl)phenyl]-1H-pyrazole-4-carboxamide (III-13) N-[2-(1,3-dimethylbutyl)phenyl]-2-iodobenzamide (III-15) N-[2-(1,3-dimethylbutyl)phenyl]-2-(trifluoromethyl)benzamide (III-18) boscalid (III-21) penthiopyrad (III-22) N-[2-(1,3-dimethylbutyl)phenyl]-1-methyl-4-(trifluoromethyl)-1H-pyrrole-3-carboxamide (III-23) N-(3',4'-dichloro-5-fluoro-1,1'-biphenyl-2-yl)-3-(difluoromethyl)-1-methyl-1H-pyrazole-4-carboxamide (III-29) N-(4'-bromo-1,1'-biphenyl-2-yl)-4-(difluoromethyl)-2-methyl-1,3-thiazole-5-carboxamide (III-31) N-(4'-iodo-1,1'-biphenyl-2-yl)-4-(difluoromethyl)-2-methyl-1,3-thiazole-5-carboxamide (III-32) N-(4'-chloro-3'-fluoro-1,1'-biphenyl-2-yl)-2-methyl-4-(difluoromethyl)-1,3-thiazole-5-carboxamide Formula (III) comprises the following particularly preferred mixing partners from the group of the carboxamides:

(III-2) N-[2-(1,3-dimethylbutyl)phenyl]-5-fluoro-1,3-dimethyl-1H-pyrazole-4-carboxamide (III-8) 5-fluoro-1,3-dimethyl-N-[2-(1,3,3-trimethylbutyl)phenyl]-1H-pyrazole-4-carboxamide (III-13) N-[2-(1,3-dimethylbutyl)phenyl]-2-iodobenzamide (III-15) N-[2-(1,3-dimethylbutyl)phenyl]-2-(trifluoromethyl)benzamide (III-23) N-(3',4'-dichloro-5-fluoro-1,1'-biphenyl-2-yl)-3-(difluoromethyl)-1-methyl-1H-pyrazole-4-carboxamide (III-31) N-(4'-iodo-1,1'-biphenyl-2-yl)-4-(difluoromethyl)-2-methyl-1,3-thiazole-5-carboxamide (III-32) N-(4'-chloro-3'-fluoro-1,1'-biphenyl-2-yl)-2-methyl-4-(difluoromethyl)-1,3-thiazole-5-carboxamide.

Active substance combinations according to the invention which are emphasized are those which, in addition to spiroxamine and (II-15) prothioconazole comprises a carboxamide selected among (III-2) N-[2-(1,3-dimethylbutyl)phenyl]-5-fluoro-1,3-dimethyl-1H-pyrazole-4-carboxamide, (III-8) 5-fluoro-1,3-dimethyl-N-[2-(1,3,3-trimethylbutyl)phenyl]-1H-pyrazole-4-carboxamide, (III-13) N-[2-(1,3-dimethylbutyl)phenyl]-2-iodobenzamide, (III-15) N-[2-(1,3-dimethylbutyl)phenyl]-2-(trifluoromethyl)benzamide, (III-23) N-(3',4'-dichloro-5-fluoro-1,1'-biphenyl-2-yl)-3-(difluoromethyl)-1-methyl-1H-pyrazole-4-carboxamide and (III-32) N-(4'-chloro-3'-fluoro-1,1'-biphenyl-2-yl)-2-methyl-4-(difluoromethyl)-1,3-thiazole-5-carboxamide.

The table which follows mentions active substance combinations which are emphasized, each of which contains at least three active substances from the abovementioned groups (A), (B) and (C).

TABLE 1

| No. | Active substance (A) | Active substance (B) | Active substance (C) |
|---|---|---|---|
| 1 | spiroxamine | (II-15) prothioconazole | (III-2) N-[2-(1,3-dimethylbutyl)phenyl]-5-fluoro-1,3-dimethyl-1H-pyrazole-4-carboxamide |
| 2 | spiroxamine | (II-17) tebuconazole | (III-2) N-[2-(1,3-dimethylbutyl)phenyl]-5-fluoro-1,3-dimethyl-1H-pyrazole-4-carboxamide |
| 3 | spiroxamine | (II-21) bitertanol | (III-2) N-[2-(1,3-dimethylbutyl)phenyl]-5-fluoro-1,3-dimethyl-1H-pyrazole-4-carboxamide |
| 4 | spiroxamine | (II-22) triadimenol | (III-2) N-[2-(1,3-dimethylbutyl)phenyl]-5-fluoro-1,3-dimethyl-1H-pyrazole-4-carboxamide |
| 5 | spiroxamine | (II-24) fluquinconazole | (III-2) N-[2-(1,3-dimethylbutyl)phenyl]-5-fluoro-1,3-dimethyl-1H-pyrazole-4-carboxamide |
| 6 | spiroxamine | (II-15) prothioconazole | (III-8) 5-fluoro-1,3-dimethyl-N-[2-(1,3,3-trimethylbutyl)phenyl]-1H-pyrazole-4-carboxamide |
| 7 | spiroxamine | (II-17) tebuconazole | (III-8) 5-fluoro-1,3-dimethyl-N-[2-(1,3,3-trimethylbutyl)phenyl]-1H-pyrazole-4-carboxamide |
| 8 | spiroxamine | (II-21) bitertanol | (III-8) 5-fluoro-1,3-dimethyl-N-[2-(1,3,3-trimethylbutyl)phenyl]-1H-pyrazole-4-carboxamide |
| 9 | spiroxamine | (II-22) triadimenol | (III-8) 5-fluoro-1,3-dimethyl-N-[2-(1,3,3-trimethylbutyl)phenyl]-1H-pyrazole-4-carboxamide |
| 10 | spiroxamine | (II-24) fluquinconazole | (III-8) 5-fluoro-1,3-dimethyl-N-[2-(1,3,3-trimethylbutyl)phenyl]-1H-pyrazole-4-carboxamide |
| 11 | spiroxamine | (II-15) prothioconazole | (III-13) N-[2-(1,3-dimethylbutyl)phenyl]-2-iodobenzamide |
| 12 | spiroxamine | (II-17) tebuconazole | (III-13) N-[2-(1,3-dimethylbutyl)phenyl]-2-iodobenzamide |
| 13 | spiroxamine | (II-21) bitertanol | (III-13) N-[2-(1,3-dimethylbutyl)phenyl]-2-iodobenzamide |
| 14 | spiroxamine | (II-22) triadimenol | (III-13) N-[2-(1,3-dimethylbutyl)phenyl]-2-iodobenzamide |
| 15 | spiroxamine | (II-24) fluquinconazole | (III-13) N-[2-(1,3-dimethylbutyl)phenyl]-2-iodobenzamide |
| 16 | spiroxamine | (II-15) prothioconazole | (III-15) N-[2-(1,3-dimethylbutyl)phenyl]-2-(trifluoromethyl)benzamide |
| 17 | spiroxamine | (II-17) tebuconazole | (III-15) N-[2-(1,3-dimethylbutyl)phenyl]-2-(trifluoromethyl)benzamide |

TABLE 1-continued

| No. | Active substance (A) | Active substance (B) | Active substance (C) |
|---|---|---|---|
| 18 | spiroxamine | (II-21) bitertanol | (III-15) N-[2-(1,3-dimethylbutyl)phenyl]-2-(trifluoromethyl)benzamide |
| 19 | spiroxamine | (II-22) triadimenol | (III-15) N-[2-(1,3-dimethylbutyl)phenyl]-2-(trifluoromethyl)benzamide |
| 20 | spiroxamine | (II-24) fluquinconazole | (III-15) N-[2-(1,3-dimethylbutyl)phenyl]-2-(trifluoromethyl)benzamide |
| 21 | spiroxamine | (II-15) prothioconazole | (III-18) boscalid |
| 22 | spiroxamine | (II-17) tebuconazole | (III-18) boscalid |
| 23 | spiroxamine | (II-21) bitertanol | (III-18) boscalid |
| 24 | spiroxamine | (II-22) triadimenol | (III-18) boscalid |
| 25 | spiroxamine | (II-24) fluquinconazole | (III-18) boscalid |
| 26 | spiroxamine | (II-15) prothioconazole | (III-21) penthiopyrad |
| 27 | spiroxamine | (II-17) tebuconazole | (III-21) penthiopyrad |
| 28 | spiroxamine | (II-21) bitertanol | (III-21) penthiopyrad |
| 29 | spiroxamine | (II-22) triadimenol | (III-21) penthiopyrad |
| 30 | spiroxamine | (II-24) fluquinconazole | (III-21) penthiopyrad |
| 31 | spiroxamine | (II-15) prothioconazole | (III-22) N-[2-(1,3-dimethylbutyl)phenyl]-1-methyl-4-(trifluoromethyl)-1H-pyrrole-3-carboxamide |
| 32 | spiroxamine | (II-17) tebuconazole | (III-22) N-[2-(1,3-dimethylbutyl)phenyl]-1-methyl-4-(trifluoromethyl)-1H-pyrrole-3-carboxamide |
| 33 | spiroxamine | (II-21) bitertanol | (III-22) N-[2-(1,3-dimethylbutyl)phenyl]-1-methyl-4-(trifluoromethyl)-1H-pyrrole-3-carboxamide |
| 34 | spiroxamine | (II-22) triadimenol | (III-22) N-[2-(1,3-dimethylbutyl)phenyl]-1-methyl-4-(trifluoromethyl)-1H-pyrrole-3-carboxamide |
| 35 | spiroxamine | (II-24) fluquinconazole | (III-22) N-[2-(1,3-dimethylbutyl)phenyl]-1-methyl-4-(trifluoromethyl)-1H-pyrrole-3-carboxamide |
| 36 | spiroxamine | (II-15) prothioconazole | (III-23) N-(3',4'-dichloro-5-fluoro-1,1'-biphenyl-2-yl)-3-(difluoromethyl)-1-methyl-1H-pyrazole-4-carboxamide |
| 37 | spiroxamine | (II-17) tebuconazole | (III-23) N-(3',4'-dichloro-5-fluoro-1,1'-biphenyl-2-yl)-3-(difluoromethyl)-1-methyl-1H-pyrazole-4-carboxamide |
| 38 | spiroxamine | (II-21) bitertanol | (III-23) N-(3',4'-dichloro-5-fluoro-1,1'-biphenyl-2-yl)-3-(difluoromethyl)-1-methyl-1H-pyrazole-4-carboxamide |
| 39 | spiroxamine | (II-22) triadimenol | (III-23) N-(3',4'-dichloro-5-fluoro-1,1'-biphenyl-2-yl)-3-(difluoromethyl)-1-methyl-1H-pyrazole-4-carboxamide |
| 40 | spiroxamine | (II-24) fluquinconazole | (III-23) N-(3',4'-dichloro-5-fluoro-1,1'-biphenyl-2-yl)-3-(difluoromethyl)-1-methyl-1H-pyrazole-4-carboxamide |
| 41 | spiroxamine | (II-15) prothioconazole | (III-29) N-(4'-bromo-1,1'-biphenyl-2-yl)-4-(difluoromethyl)-2-methyl-1,3-thiazole-5-carboxamide |
| 42 | spiroxamine | (II-17) tebuconazole | (III-29) N-(4'-bromo-1,1'-biphenyl-2-yl)-4-(difluoromethyl)-2-methyl-1,3-thiazole-5-carboxamide |
| 43 | spiroxamine | (II-21) bitertanol | (III-29) N-(4'-bromo-1,1'-biphenyl-2-yl)-4-(difluoromethyl)-2-methyl-1,3-thiazole-5-carboxamide |
| 44 | spiroxamine | (II-22) triadimenol | (III-29) N-(4'-bromo-1,1'-biphenyl-2-yl)-4-(difluoromethyl)-2-methyl-1,3-thiazole-5-carboxamide |
| 45 | spiroxamine | (II-24) fluquinconazole | (III-29) N-(4'-bromo-1,1'-biphenyl-2-yl)-4-(difluoromethyl)-2-methyl-1,3-thiazole-5-carboxamide |
| 46 | spiroxamine | (II-15) prothioconazole | (III-31) N-(4'-iodo-1,1'-biphenyl-2-yl)-4-(difluoromethyl)-2-methyl-1,3-thiazole-5-carboxamide |
| 47 | spiroxamine | (II-17) tebuconazole | (III-31) N-(4'-iodo-1,1'-biphenyl-2-yl)-4-(difluoromethyl)-2-methyl-1,3-thiazole-5-carboxamide |
| 48 | spiroxamine | (II-21) bitertanol | (III-31) N-(4'-iodo-1,1'-biphenyl-2-yl)-4-(difluoromethyl)-2-methyl-1,3-thiazole-5-carboxamide |
| 49 | spiroxamine | (II-22) triadimenol | (III-31) N-(4'-iodo-1,1'-biphenyl-2-yl)-4-(difluoromethyl)-2-methyl-1,3-thiazole-5-carboxamide |
| 50 | spiroxamine | (II-24) fluquinconazole | (III-31) N-(4'-iodo-1,1'-biphenyl-2-yl)-4-(difluoromethyl)-2-methyl-1,3-thiazole-5-carboxamide |
| 51 | spiroxamine | (II-15) prothioconazole | (III-32) N-(4'-chloro-3'-fluoro-1,1'-biphenyl-2-yl)-2-methyl-4-(difluoromethyl)-1,3-thiazole-5-carboxamide |
| 52 | spiroxamine | (II-17) tebuconazole | (III-32) N-(4'-chloro-3'-fluoro-1,1'-biphenyl-2-yl)-2-methyl-4-(difluoromethyl)-1,3-thiazole-5-carboxamide |

TABLE 1-continued

| No. | Active substance (A) | Active substance (B) | Active substance (C) |
|---|---|---|---|
| 53 | spiroxamine | (II-21) bitertanol | (III-32) N-(4'-chloro-3'-fluoro-1,1'-biphenyl-2-yl)-2-methyl-4-(difluoromethyl)-1,3-thiazole-5-carboxamide |
| 54 | spiroxamine | (II-22) triadimenol | (III-32) N-(4'-chloro-3'-fluoro-1,1'-biphenyl-2-yl)-2-methyl-4-(difluoromethyl)-1,3-thiazole-5-carboxamide |
| 55 | spiroxamine | (II-24) fluquinconazole | (III-32) N-(4'-chloro-3'-fluoro-1,1'-biphenyl-2-yl)-2-methyl-4-(difluoromethyl)-1,3-thiazole-5-carboxamide |

In addition to the active substance (A) spiroxamine, the active substance combinations according to the invention comprise an active substance (B) of the formula (II) and an active substance (C) of the formula (III). They can furthermore additionally comprise other fungicidally active components for admixture.

The synergistic effect is particularly pronounced when the active substances are present in certain weight ratios in the active substance combinations according to the invention. However, the weight ratios of the active substances in the active substance combinations can be varied within a relatively wide range. In general, 0.05 to 20 parts by weight, preferably 0.1 to 10 parts by weight, of active substance (B) of the formula (II) and 0.02 to 50 parts by weight, preferably 0.05 to 20 parts by weight, especially preferably 0.1 to 10 parts by weight of active substance (C) of the formula (III) are used per part by weight of active substance (A) spiroxamine. The mixing ratio is preferably to be selected in such a way that a synergistic mixture is obtained.

The active substance combinations according to the invention have very good fungicidal properties and can be employed for controlling phytopathogenic fungi such as Plasmodiophoromycetes, Oomycetes, Chytridiomycetes, Zygomycetes, Ascomycetes, Basidiomycetes, Deuteromycetes and the like.

The active substance combinations according to the invention are particularly suitable for controlling *Erysiphe graminis, Pyrenophora teres* and *Leptosphaeria nodorum*.

Nonlimiting examples of some causative agents of fungal diseases which come under the generic names detailed above may be mentioned:

*Pythium* species such as, for example, *Pythium ultimum; Phytophthora* species such as, for example, *Phytophthora infestans; Pseudoperonospora* species such as, for example, *Pseudoperonospora humuli* or *Pseudoperonospora cubensis; Plasmopara* species such as, for example, *Plasmopara viticola; Bremia* species such as, for example, *Bremia lactucae; Peronospora* species such as, for example, *Peronospora pisi* or *P. brassicae; Erysiphe* species such as, for example, *Erysiphe graminis; Sphaerotheca* species such as, for example, *Sphaerotheca fuliginea; Podosphaera* species such as, for example, *Podosphaera leucotricha; Venturia* species such as, for example, *Venturia inaequalis; Pyrenophora* species such as, for example, *Pyrenophora teres* or *P. graminea* (conidial form *Drechslera*, syn: *Helminthosporium*); *Cochliobolus* species such as, for example, *Cochliobolus sativus* (conidial form: *Drechslera*, syn: *Helminthosporium*); *Uromyces* species such as, for example, *Uromyces appendiculatus; Puccinia* species such as, for example, *Puccinia recondita; Sclerotinia* species such as, for example, *Sclerotinia sclerotiorum; Tilletia* species such as, for example, *Tilletia caries; Ustilago* species such as, for example, *Ustilago nuda* or *Ustilago avenae; Pellicularia* species such as, for example, *Pellicularia sasakii; Pyricularia* species such as, for example, *Pyricularia oryzae; Fusarium* species such as, for example, *Fusarium culmorum; Botrytis* species such as, for example, *Botrytis cinerea; Septoria* species such as, for example, *Septoria nodorum; Leptosphaeria* species such as, for example, *Leptosphaeria nodorum; Cercospora* species such as, for example, *Cercospora canescens; Alternaria* species such as, for example, *Alternaria brassicae; Pseudocercosporella* species such as, for example, *Pseudocercosporella herpotrichoides, Rhizoctonia* species such as, for example, *Rhizoctonia solani*.

The good tolerance, by plants, of the active substance combinations at the concentrations required for controlling plant diseases permits the treatment of intact plants (aerial plant parts and roots), of vegetative propagation material and seed, and of the soil. The active substance combinations according to the invention can be employed for foliar application or else as seed-dressing agents.

The good tolerance, by plants, of the active substances which can be used, at the concentrations required for controlling plant diseases, permits the treatment of seed. As a consequence, the active substances according to the invention can be employed as seed-dressing agents.

A large part of the crop plant damage caused by phytopathogenic fungi is the result of the seed already being attacked during storage and after the seed has been introduced into the soil, and during and immediately after germination of the plants. This phase is particularly critical since the roots and shoots of the growing plant are particularly sensitive and even a minor degree of damage can lead to the death of the entire plant. There is therefore in particular a great interest in protecting the seed and the terminating plant by using suitable compositions.

The control of phytopathogenic fungi which damage plants after emergence is mainly accomplished by treating the soil and the aerial plant parts with plant protection products. As a result of reservations regarding a potential effect of the plant protection on the environment and the health of humans and animals, attempts are being made to reduce the amount of the active substances which are applied.

The control of phytopathogenic fungi by the treatment of the seed of plants has long been known and is the subject of continuous improvement. However, the treatment of seed leads to a series of problems which cannot always be solved satisfactorily. By the dry seed treatment method, by using a solution for seed treatment, a water-soluble powder for seed treatment or a water-dispersible powder, the treatment of seed leads to a series of problems which cannot always be solved satisfactorily. Thus, it is desirable to develop methods of protecting the seed and the germinating plant which do away with, or at least substantially reduce, the additional application of crop protection products after sowing or after the emergence of the plants. Moreover it is desirable to optimize the amount of the active substance employed in such a way that the seed and the germinating plant are protected as best as possible against attack by phytopathogenic fungi without the plant itself being damaged by the active substance employed. In particular, methods for the treatment of seed should also incorporate the intrinsic fungicidal properties of transgenic plants in order to achieve an optimal protection of the seed and of the germinating plant while applying the minimum amount of plant protection products.

The present invention therefore particularly also relates to a method of protecting seed and germinating plants against attack by phytopathogenic fungi, by treating the seed with a composition according to the invention.

The invention also relates to the use of the compositions according to the invention for the treatment of seed for protecting the seed and the germinating plant from phytopathogenic fungi.

Furthermore, the invention relates to seed which has been treated with a composition according to the invention as protection from phytopathogenic fungi.

One of the advantages of the present invention is that, as the result of the specific systemic properties of the compositions according to the invention, the treatment of the seed with these compositions protects not only the seed itself, but also, after emergence, the plants which the seeds give rise to, against phytopathogenic fungi. In this manner, the immediate treatment of the crop at the point in time of sowing or shortly thereafter can be dispensed with.

Equally, it can be seen as advantageous that the mixtures according to the invention can also be employed in particular in transgenic seed.

The compositions according to the invention are suitable for the protection of seed of any plant variety which is employed in agriculture, in the greenhouse, in forests or in horticulture. In particular, this takes the form of seed of cereals (such as wheat, barley, rye, sorghum/millet and oats), maize, cotton, soybeans, rice, potatoes, sunflower, bean, coffee, beet (for example sugar beet and fodder beet), peanut, vegetables (such as tomato, cucumber, onions and lettuce), turf and ornamentals. The treatment of the seed of cereals (such as wheat, barley, rye and oats), maize and rice is of particular importance.

For the purposes of the present invention, the composition according to the invention is applied to the seed on its own or in a suitable formulation. Preferably, the seed is treated in a state in which it is sufficiently stable to avoid damage upon the treatment. In general, the treatment of the seed can be effected at any point in time between harvesting and sowing. Usually, seed will be used which has been separated from the plant and freed from cobs, husks, stems, hull, fiber or pulp. Thus, for example, seed can be used which has been harvested, cleaned and dried down to a moisture content of less than 15% by weight. Alternatively, it is also possible to use seed which, after drying, has been treated for example with water and then redried.

In general, care must be taken when treating the seed that the amount of the composition according to the invention and/or of further additives applied to the seed is selected in such a way that the germination of the seed is not adversely affected, or that the plant which the seed gives rise to is not damaged. This must be considered in particular in the case of active substances which can lead to phytotoxic effects at certain application rates.

The compositions according to the invention can be applied directly, that is to say without comprising further components and without having been diluted. As a rule, it is preferred to apply the compositions to the seed in the form of a suitable formulation. Suitable formulations and methods for the treatment of seed are known to the skilled worker and are described for example in the following documents: U.S. Pat. Nos. 4,272,417 A, 4,245,432 A, 4,808,430 A, 5,876,739 A, US 2003/0176428 A1, WO 2002/080675 A1, WO 2002/028186 A2.

The active substance combinations according to the invention are also suitable for increasing the yield. Moreover, they show a low degree of toxicity and are well tolerated by plants.

All plants and plant parts can be treated in accordance with the invention. In the present context, plants are understood as meaning all plants and plant populations, such as desired and undesired wild plants or crop plants (including naturally occurring crop plants). Crop plants can be plants which can be obtained by traditional breeding and optimization methods or by biotechnological and recombinant methods, or combinations of these methods, including the transgenic plants and including the plant varieties capable or not of being protected by Plant Breeders' Rights. Plant parts are understood as meaning all aerial and subterranean parts and organs of the plants, such as shoot, leaf, flower and root, examples which may be mentioned being leaves, needles, stalks, stems, flowers, fruiting bodies, fruits and seeds, and also roots, tubers and rhizomes. The plant parts also include harvested material and vegetative and generative propagation material, for example cuttings, tubers, rhizomes, slips and seeds.

The treatment according to the invention of the plants and plant parts with the active substances is accomplished directly or by acting on their surroundings, environment or storage space, using the customary treatment methods, for example by dipping, spraying, vaporizing, fogging, scattering, brushing on and, in the case of propagation material, in particular seeds, furthermore by coating with one or more coats.

As already mentioned above, all plants and their parts can be treated in accordance with the invention. In a preferred embodiment, plant species and plant varieties which are found in the wild or are obtained by traditional biological breeding methods, such as hybridization or protoplast fusion, and parts of the former are treated. In a further preferred embodiment, transgenic plants and plant varieties which have been obtained by recombinant methods, if appropriate in combination with traditional methods (genetically modified organisms) and their parts are treated. The term "parts" or "parts of plants" or "plant parts" has been illustrated above.

Particularly preferably, plants of the plant cultivars which are in each case commercially available or in use are treated according to the invention.

Depending on the plant species or plant cultivars, their location and growth conditions (soils, climate, vegetation period, nutrition), the treatment according to the invention may also result in superadditive ("synergistic") effects. Thus, for example, reduced application rates and/or extensions of the activity spectrum and/or an increase in the activity of the substances and compositions that can be used according to the invention, better plant growth, increased tolerance to high or low temperatures, increased tolerance to drought or to water or soil salinity, increased flowering performance, easier harvesting, accelerated maturation, higher yields, better quality and/or a higher nutritional value of the harvested products, better storage ability and/or processibility of the harvested products which exceed the effects which were actually to be expected are possible.

The preferred transgenic plants or plant cultivars (i.e. those obtained by genetic engineering) which are to be treated according to the invention include all plants which, as a result of the recombinant modification, received genetic material which imparted particularly advantageous useful properties ("traits") to these plants. Examples of such properties are better plant growth, increased tolerance to high or low temperatures, increased tolerance to drought or to water or soil salinity, increased flowering performance, easier harvesting, accelerated maturation, higher yields, better quality and/or a higher nutritional value of the harvested products, better storage ability and/or processibility of the harvested products. Further and particularly emphasized examples of such properties are a better defence of the plants against animal and microbial pests, such as against insects, mites, phytopathogenic fungi, bacteria and/or viruses, and also increased tolerance of the plants to certain herbicidally active substances. Examples of transgenic plants which may be mentioned are the important crop plants, such as cereals (wheat, rice), maize, soybeans, potatoes, cotton, oilseed rape and also fruit plants (with the fruits apples, pears, citrus fruits and grapes), and particular emphasis is given to maize, soybeans, potatoes, cotton and oilseed rape. Traits that are emphasized in particular are increased defence of the plants against insects as the result of toxins formed in the plants, in particular those formed in the plants by the genetic material from *Bacillus thuringiensis* (for example by the genes CryIA(a), CryIA(b), CryIA(c), CryIIA, CryIIIA, CryIIIB2, Cry9c, Cry2Ab, Cry3Bb and CryIF and also combinations thereof) (hereinbelow referred to as "Bt plants"). Traits that are furthermore particularly emphasized are the increased tolerance of the plants to certain herbicidally active substances, for example imidazolinones, sulfonylureas, glyphosate or phosphinothricin (for example the "PAT" gene). The genes which impart the desired traits in question can also be present in combinations with one another in the transgenic plants. Examples of "Bt plants" which may be mentioned are maize varieties, cotton varieties, soybeans varieties and potato varieties which are sold under the trade names YIELD GARD® (for example maize, cotton, soybeans), KnockOut® (for example maize), StarLink® (for example maize), Bollgard® (cotton), Nucoton® (cotton) and NewLeaf® (potato). Examples of herbicide-tolerant plants which may be mentioned are maize varieties, cotton varieties and soybeans varieties which are sold under the trade names Roundup Ready® (tolerance to glyphosates, for example maize, cotton, soybeans), Liberty Link® (tolerance to phosphinothricin, for example oilseed rape), IMI® (tolerance to imidazolinones) and STS® (tolerance to sulfonylureas, for example maize). Herbicide-resistant plants (plants bred in a conventional manner for herbicide tolerance) which may be mentioned also include the varieties sold under the name Clearfield® (for example maize). Of course, these statements also apply to plant varieties which are developed in the future, or will be commercially available in the future, and which have these genetic traits or genetic traits yet to be developed.

Depending on their particular physical and/or chemical properties, the active substance combinations according to the invention can be converted into the customary formulations, such as solutions, emulsions, suspensions, powders, dusts, foams, pastes, soluble powders, granules, aerosols, suspoemulsion concentrates, natural and synthetic materials which are impregnated with active substance, and microencapsulations in polymeric substances and in coating compositions for seed, and ULV cold- and warm-fogging formulations.

These formulations are prepared in a known manner, for example by mixing the active substances, or the active substance combinations, with extenders, that is liquid solvents, pressurized liquefied gases and/or solid carriers, if appropriate using surface-active agents, that is emulsifiers and/or dispersants and/or foam formers.

If water is used as extender, it is also possible for example to use organic solvents as cosolvents. Liquid solvents which are suitable are essentially: aromatics such as xylene, toluene or alkylnaphthalenes, chlorinated aromatics or chlorinated aliphatic hydrocarbons such as chlorobenzenes, chloroethylenes or methylene chloride, aliphatic hydrocarbons such as cyclohexane or paraffins, for example mineral oil fractions, mineral and vegetable oils, alcohols such as butanol or glycol and their ethers and esters, ketones, such as acetone, methyl ethyl ketone, methyl isobutyl ketone or cyclohexanone, strongly polar solvents such as dimethylformamide and dimethyl sulfoxide, and water.

Liquefied gaseous extenders or carriers are understood as meaning those liquids which are gaseous at normal temperature and under atmospheric pressure, for example aerosol propellants such as butane, propane, nitrogen and carbon dioxide.

Solid carriers which are suitable are: for example ammonium salts and ground natural minerals such as kaolins, clays, talc, chalk quartz, attapulgite, montmorillonite or diatomaceous earth, and ground synthetic minerals, such as highly disperse silica, alumina and silicates. Solid carriers for granules which are suitable are: for example crushed and fractionated natural rocks such as calcite, marble, pumice, sepiolite, dolomite and synthetic granules of organic and inorganic meals, and granules of organic material such as sawdust, coconut shells, maize cobs and tobacco stalks. Suitable emulsifiers and/or foam formers are: for example nonionic and anionic emulsifiers such as polyoxyethylene fatty acid esters, polyoxyethylene fatty alcohol ethers, for example alkylaryl polyglycol ethers, alkylsulfonates, alkyl sulfates, arylsulfonates and protein hydrolyzates. Dispersants which are suitable are: for example lignin-sulfite waste liquors and methylcellulose.

Adhesives such as carboxymethylcellulose, natural and synthetic polymers in the form of powders, granules or latices such as gum arabic, polyvinyl alcohol, polyvinyl acetate, and natural phospholipids such as cephalins and lecithins, and synthetic phospholipids, can be used in the formulations. Other additives can be mineral and vegetable oils.

It is possible to use colorants such as inorganic pigments, for example iron oxide, titanium oxide, Prussian blue, and organic dyestuffs such as alizarin, azo and metal phthalocyanin dyestuffs and trace nutrients such as salts of iron, manganese, boron, copper, cobalt, molybdenum and zinc.

The active substance content of the use forms prepared from the commercially available formulations can vary within wide limits. The active substance concentration of the use forms for controlling animal pests such as insects and acarids can range from 0.0000001 to 95% by weight of active substance, preferably between 0.0001 and 1% by weight. The application is accomplished in a customary manner adapted to the use forms.

The formulations for controlling undesired phytopathogenic fungi generally comprise between 0.1 and 95% by weight of active substances, preferably between 0.5 and 90%.

The active substance combinations according to the invention can be applied as such, in the form of their formulations or the use forms prepared therefrom, such as ready-to-use solutions, emulsifiable concentrates, emulsions, suspensions, wettable powders, soluble powders, dusts and granules. They are applied in a customary manner, for example by drenching, trickle irrigation, spraying, atomizing, scattering, dusting, foaming, painting on, brushing on, by the dry seed treatment, by seed treatment with a solution, a water-soluble powder or a water-dispersible powder, by encrusting and the like.

In commercially available formulations and in the use forms prepared from these formulations, the active substance combinations according to the invention can be present as a mixture with other active substances such as insecticides, attractants, sterilants, bactericides, acaricides, nematicides, fungicides, growth regulators or herbicides.

When using the active substance combinations according to the invention, the application rates can be varied within a substantial range, depending on the type of application. In the treatment of plant parts, the application rates of active substance combination are generally between 0.1 and 10 000 g/ha, preferably between 10 and 1000 g/ha. In the treatment of seed, the application rates of active substance combination are generally between 0.001 and 50 g per kilogram of seed, preferably between 0.01 and 10 g per kilogram of seed. In the treatment of the soil, the application rates of active substance combination are generally between 0.1 and 10 000 g/ha, preferably between 1 and 5000 g/ha.

The active substance combinations can be employed as such, in the form of concentrates or generally customary formulations such as powders, granules, solutions, suspensions, emulsions or pastes.

The abovementioned formulations can be prepared in a manner known per se, for example by mixing the active substances with at least one solvent or diluent, emulsifier, dispersant and/or binder or fixative, water repellant, if appropriate desiccants and UV stabilizers and, if appropriate, colorants and pigments and further processing auxiliaries.

The good fungicidal activity of the active substance combinations according to the invention can be seen from the examples which follow. While the individual active substances show weaknesses in their fungicidal activity, the combinations display an effect which exceeds a simple sum of activities.

The invention is illustrated by the examples which follow. However, the invention is not limited to the examples.

USE EXAMPLE

*Pyrenophora teres* Test (Barley)/shoot Treatment, Field Experiment

To prepare a suitable preparation of active substance, a "commercially available" formulation of active substance or active substance combination is diluted with water to give the desired concentration.

The active substance preparation is applied at the application rate stated, after the flag leaf has emerged.

The evaluation is carried out at the point in time at which the disease symptoms are complete and readily recognizable. In this context, 0% means an efficacy which corresponds to that of the control, while an efficacy of 100% means that no disease is observed.

To demonstrate synergism between the active substances used in this experiment, the results were evaluated by the method described by R. S. Colby (Calculating Synergistic and Antagonistic Responses of Herbicides Combinations; Weeds 1967, 15, 20-22). The expected efficacy in % of the untreated control was calculated using the equation $$E = X + Y - \frac{X \times Y}{100}.$$

In this equation, x and y mean the efficacy—expressed in % of the untreated control—which the two products achieve when applied separately. If the actual efficacy of the active substance combination exceeds the value for the expected efficacy (E) as calculated by the above formula, then the effect is superadditive, i.e. a synergistic effect exists.

TABLE

*Pyrenophora teres* test (barley)/shoot treatment, field experiment

| Active substance | Application rate of active substance in g/ha | Efficacy in % found* | expected (E) |
|---|---|---|---|
| Known: | | | |
| (III-23) N-(3',4'-dichloro-5-fluoro-1,1'-biphenyl-2-yl)-3-(difluoromethyl)-1-methyl-1H-pyrazole-4-carboxamide | 62.5 | 40 | |
| prothioconazole + spiroxamine | 575 (200 + 375) | 12 | |
| Mixture according to the invention: | | | |
| (III-23) N-(3',4'-dichloro-5-fluoro-1,1'-biphenyl-2-yl)-3-(difluoromethyl)-1-methyl-1H-pyrazole-4-carboxamide + prothioconazole + spiroxamine | 62.5 + 100 + 188 | 93 | <47 |

*Scoring: long-term effect, 41 days post-application

We claim:

1. A composition comprising spiroxamine, (II-15) prothioconazole, and (III-23) N-(3',4'-dichloro-5-fluoro-1,1'-biphenyl-2-yl)-3-(difluoromethyl)-1-methyl-1H-pyrazole-4-carboxamide.

2. A method of controlling undesired phytopathogenic fungi comprising contacting said fungi with a composition according to claim 1.

3. A method of controlling undesired phytopathogenic fungi comprising treating plant seed with a composition according to claim 1.

4. A method of controlling undesired phytopathogenic fungi in transgenic plants comprising treating said plants with a composition according to claim 1.

5. A method of controlling undesired phytopathogenic fungi in transgenic plant seed comprising treating said seed with a composition according to claim 1.

6. Seed which has been treated with a composition according to claim 1.

7. A method of controlling undesired phytopathogenic fungi, comprising applying a composition according to claim 1 to the undesired phytopathogenic fungi, their environment, seed, or a combination thereof.

8. A process for the preparation of fungicidal compositions, comprising mixing a composition according to claim 1 with extenders, surface-active substances, or mixtures thereof.

9. The composition according to claim 1 wherein the ratio of spiroxamine to prothioconazole is from 1:0.05 to 1:20.

10. The composition according to claim 9 wherein the ratio of spiroxamine to prothioconazole is from 1:0.1 to 1:10.

11. The composition according to claim 1 wherein the ratio of spiroxamine to N-(3',4'-dichloro-5-fluoro-1,1'-biphenyl-2-yl)-3-(difluoromethyl)-1-methyl-1H-pyrazole-4-carboxamide is from 1:0.02 to 1:50.

12. The composition according to claim 11 wherein the ratio of spiroxamine to N-(3',4'-dichloro-5-fluoro-1,1'-biphenyl-2-yl)-3 -(difluoromethyl)-1-methyl-1H-pyrazole-4-carboxamide is from 1:0.05 to 1:20.

13. The composition according to claim 12 wherein the ratio of spiroxamine to N-(3',4'-dichloro-5-fluoro-1,1'-biphenyl-2-yl)-3-(difluoromethyl)-1-methyl-1H-pyrazole-4-carboxamide is from 1:0.1 to 1:10.

14. The composition according to claim 1 wherein the ratio of spiroxamine to prothioconazole to N-(3',4'-dichloro-5-fluoro-1,1'-biphenyl-2-yl)-3-(difluoromethyl)-1-methyl-1H-pyrazole-4-carboxamide is 188:100:62.5.

15. The composition according to claim 1 which is synergistic.

16. The method according to claim 2 wherein the undesired phytopathogenic fungi are *Pyrenophora* species.

17. The method according to claim 16 wherein the *Pyrenophora* species is *Pyrenophora teres*.

18. The method according to claim 2 wherein the composition is applied at a rate of between 10 and 1000 g/ha.

* * * * *